United States Patent [19]
Guthrie, Jr. et al.

[11] Patent Number: 5,169,120
[45] Date of Patent: Dec. 8, 1992

[54] ZERO DEAD VOLUME VARIABLE RESTRICTOR

[75] Inventors: James W. Guthrie, Jr., Nottingham; Steven M. Lurcott, Avondale, both of Pa.

[73] Assignee: Computer Chemical Systems, Inc., Avondale, Pa.

[21] Appl. No.: 486,055

[22] Filed: Feb. 27, 1990

[51] Int. Cl.$^5$ .................. F16K 13/00; F16K 51/00
[52] U.S. Cl. ........................ 251/122; 138/45
[58] Field of Search ............ 251/4, 8, 120, 121, 251/122, 123; 138/45; 285/342, 343

[56] References Cited

U.S. PATENT DOCUMENTS

| | | | |
|---|---|---|---|
| 1,657,663 | 1/1928 | Devereux | 251/4 |
| 2,442,746 | 6/1948 | Anderson et al. | 251/4 |
| 2,909,376 | 10/1959 | Drew | 285/342 |
| 3,016,250 | 1/1962 | Franck | 285/342 |
| 3,072,151 | 1/1963 | Quercia | 138/45 |
| 3,095,175 | 6/1963 | Iketani | 251/4 |
| 3,266,824 | 8/1966 | Nealy | 285/342 |
| 3,685,786 | 8/1972 | Woodson | 251/4 |
| 4,105,050 | 8/1978 | Hendrickson et al. | 138/45 |
| 4,109,895 | 8/1978 | Smart, Jr. et al. | 251/4 |
| 4,281,679 | 8/1981 | Stearns | 285/342 |
| 4,458,927 | 7/1984 | Smith | 285/342 |
| 4,703,775 | 11/1987 | Pastrone | 251/121 |
| 4,776,618 | 10/1988 | Barree | 285/342 |
| 4,787,656 | 11/1988 | Ryder | 285/342 |

*Primary Examiner*—George L. Walton
*Attorney, Agent, or Firm*—Louis Weinstein

[57] ABSTRACT

A variable restrictor for controlling flow rate including a ferrule formed of a yieldable material and having an opening at one end cooperating with the carrier line delivering fluid thereto. A passageway in the ferrule communicating with the carrier line terminates at the opposite end of the ferrule which is provided with a conical-shaped end portion cooperating with a recess of a conforming taper provided in a member having a passageway communicating with the utilization device receiving the fluid. The flow rate is regulated by controlling the position of the ferrule relative to the cooperating recess which controls the amount of compression exerted upon the forward end of the ferrule and hence the amount of constriction of the passageway extending therethrough. The variable restrictor assembly is provided with first external adjustment means for regulating flow rate and internal adjustment means for controlling the force exerted by a yieldable holding collet upon the carrier line to maintain the carrier line in place even in the presence of high operating pressures, the internal and external adjustment devices being capable of adjustment totally independently of one another.

14 Claims, 1 Drawing Sheet

ZERO DEAD VOLUME VARIABLE RESTRICTOR

FIELD OF THE INVENTION

The present invention relates to variable restrictors or valves and more particularly to a variable restrictor which is adjustable to achieve extremely small and hence highly accurate flow regulation and to maintain the integrity of the system even under high operating pressures.

BACKGROUND OF THE INVENTION

Manual and automated supercritical fluid extraction and chromatography systems require orifice restrictors for regulating the flow of fluid during extraction and chromatography operations. It is conventional in such apparatus to employ fixed orifice restrictors. These restrictors which are typically made of stainless steel, fused silica or ceramic are unsuitable since they tend to clog, break and/or require frequent maintenance. Furthermore, they are limited to a fixed flow rate at a given pressure/density setting thus significantly reducing the versatility of the extractor and chromatography systems.

BRIEF DESCRIPTION OF THE INVENTION

The present invention is characterized by comprising a durable, variable restrictor which minimizes clogging and is easily adjusted for flow rates over a wide pressure/density range. The automated device maintains constant flow over these wide parameter changes.

The invention is comprised of a ferrule having an opening at one end thereof communicating with a carrier line delivering fluid under pressure. The ferrule is provided with a passageway communicating with the carrier line, and terminating at the opposite end of the ferrule which is provided with a conical-shaped end portion.

A holder surrounding the ferrule and a portion of the carrier line adjacent said ferrule is provided with a tapered recess for receiving the conical-shaped portion of the ferrule. A passageway in the holder communicates with the tapered recess for delivering the fluid entering the passageway to a utilization device such as, for example, SFC chromatography equipment or an extractor employed in such equipment. Members cooperating with the holder and the ferrule are adjustable to urge the ferrule against the recess in said holder to compress the ferrule and thereby regulate the size of the opening in the passageway adjacent said conical-shaped portion.

The end of the ferrule receiving the adjacent end of the carrier line is similarly tapered and cooperates with an adapter having a conforming tapered recess which compresses the ferrule about the carrier line when tightened to create a zero dead volume seal therebetween.

In order to prevent the carrier line from experiencing any movement, especially during the presence of high operating pressures, a tapered holding collet is placed between the adapter and a cooperating adjustable assembly. The holding collet has a split configuration enabling its split halves to intimately and securely grip the portion of the carrier line passing therethrough by means of a cooperating member having a tapered recess for appropriately compressing the collet about the carrier line when the holder assembly is adjusted thereby simultaneously creating a zero dead volume seal between the ferrule and the carrier line as well as firmly gripping the carrier line to prevent any movement thereof. The flow regulation adjustment and the adjustment for sealing of the carrier line and the gripping thereof are independent of one another, thus increasing the versatility and usefulness of the variable restrictor.

Although the variable restrictor has been described as being employed within supercritical fluid extraction and chromatography apparatus, it should be understood that the restrictor may be employed in a variety of other applications such as a back pressure regulator, high pressure variable splitter, high pressure fraction collection, and liquid extraction, to name just a few.

OBJECTS OF THE INVENTION AND BRIEF DESCRIPTION OF THE FIGURES

It is therefore one object of the present invention to provide a novel variable restrictor capable of adjusting flow rate of a fluid therethrough in a highly controlled and accurate manner.

Still another object of the present invention is to provide a novel variable restrictor for regulating flow rate of a fluid passing through a carrier line in a highly accurate manner and further for creating a zero dead volume seal between the carrier line and the restrictor.

Still another object of the present invention is to provide a novel variable restrictor for regulating flow rate through a line wherein the flow rate and the securement of the carrier line may be adjustably obtained with said adjustments being independent of one another.

Still another object of the present invention is to provide a novel variable restrictor for regulating the flow of a fluid comprising a tapered member having a passageway cooperating with a passageway and a second member, said passageways communicating when said first member having a tapered conical portion, is urged into a recess of conforming shape in said second member whereby adjustment of the compression force applied between said members serves to regulate the flow through said first mentioned passageway.

Still another object of the present invention is to provide a novel variable restrictor having a member for receiving a carrier line whose flow rate is to be controlled and comprising adjustable means having a tapered recess for receiving the tapered end of said carrier line receiving member whereby said assembly applies a compression force therebetween to create a zero dead volume seal between said member and the carrier line.

The above as well as other objects of the present invention will become apparent when reading the accompanying description and drawing in which.

DETAILED DESCRIPTION OF THE INVENTION

Figure 1:
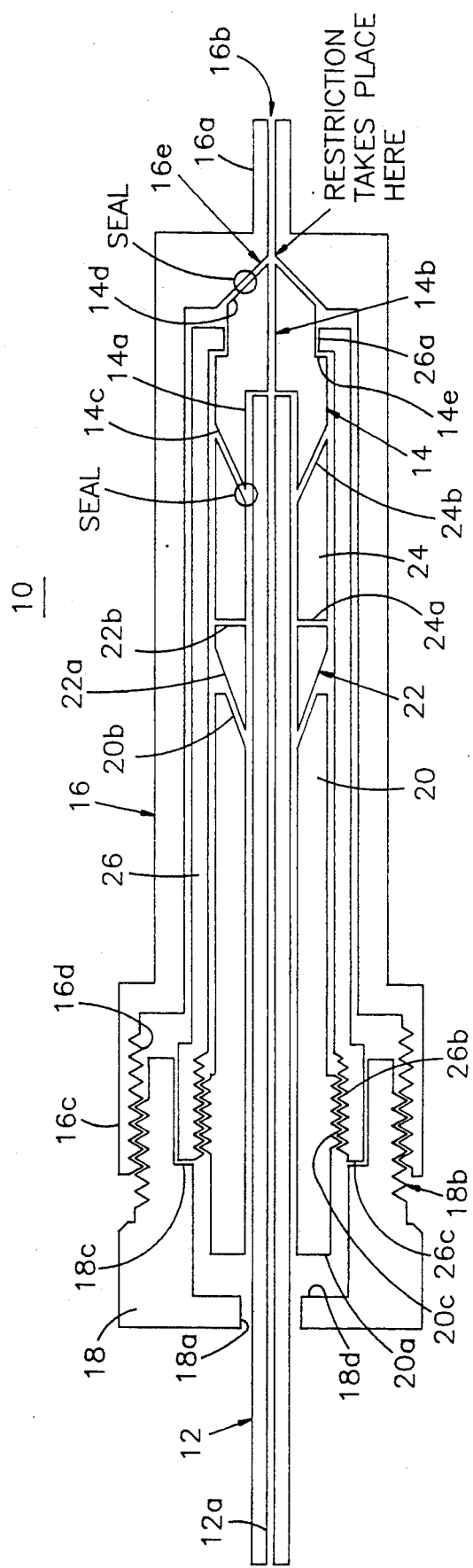
FIG. 1 shows a sectional view of a variable restrictor designed in accordance with the principles of the present invention.

The variable restrictor 10 of the present invention is presented in a sectional view in FIG. 1 and is adapted to receive the outlet end of a carrier line 12 which, in one preferred embodiment, has an outer diameter of 0.062 inches and extends into the hollow central region of restrictor assembly 10. A ferrule 14 formed of a suitable plastic such as SPI polyimide has a line receiving bore 14a whose diameter is sufficient to receive the right-hand end of carrier line 12. A passageway 14b of reduced diameter extends through ferrule 14 and communicates with the passageway 12a in carrier 12. The passageway 14b terminates at the right-hand end of ferrule 14 and its outlet end is located at the tip of a conical-shaped portion 14d. The left-hand end of ferrule 14 similarly terminates in a truncated conical-shaped portion 14c. Conical-shaped portion 14d extends into a tapered recess 16e provided within the interior of an end portion of a hollow generally cylindrical-shaped member 16 whose left-hand end 16c is of a slightly greater diameter than the main body portion thereof and is provided with a threaded portion 16d along the interior periphery for threadedly engaging the threaded portion 18b of a generally hollow cylindrical-shaped member 18 with a cap-like portion at its left-hand end provided with an opening 18a to permit carrier line 12 to pass therethrough with sufficient clearance so that the member 18 is sufficiently displaced from carrier line 12.

A hollow, substantially cylindrical-shaped adapter 24 encircles carrier line 12 and has a tapered recess 24b engaging the conical-shaped portion 14c of ferrule 14. The left-hand end of adapter 24 engages the right-hand end of split collet 22 which has a hollow interior for receiving and encircling carrier line 12. The left-hand end of collet 22 is provided with a conical-shaped portion 22a which is received within a tapered recess 20b provided within hollow cylindrical-shaped member 20 which is provided with a threaded portion 20c for threadedly engaging the threaded portion 26b of a hollow cylindrical-shaped member 26 whose left-hand end 26c rests against a shoulder 18c provided along the interior periphery of member 18 and whose right-hand end is provided with an inwardly directed annular flange 26a which cooperates with a shoulder 14e provided in ferrule 14 to exert compressive forces on members 22, 24 and 14, as will be more fully described.

The adjustment of variable restrictor assembly 10 is obtained as follows:

Although the right-hand end of carrier line 12a extends into ferrule 14, it is important to provide an adequate fluid-tight seal therebetween. This is accomplished by adjusting the threaded engagement between members 26 and 20. Ferrule 14 is maintained in position, i.e. is prevented from moving to the right relative to member 26 due to the abutment of its shoulder 14e against flange 26a. By tightening the members 20 and 26, member 20 is moved toward the right relative to member 26 urging collet 22 and adapter 24 toward the right.

Tapered recess 24b causes the conical-shaped portion 14c of ferrule 14 to be compressed about the external periphery of carrier line 12 forming an excellent zero dead volume fluid-tight seal therebetween.

Figure 2:
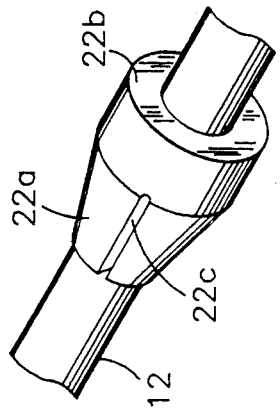
FIG. 2 shows a detailed perspective view of the holding collet of FIG. 1.

Although an adequate fluid-tight seal is obtained between members 14 and 12, it is important to prevent carrier line 12 from movement, i.e. vibration, especially under high operating pressures which can reach 10,000 psi at temperatures of up to 300° C. This holding force is obtained by split collet 22 which, from a consideration of FIG. 2, can be seen to have elongated slits diametrically opposing one another (only one of such slits 22c being shown in FIG. 2 for purposes of simplicity) whereby a compressive force exerted upon collet 22 by members 20 and 24, urges the two halves of metallic split groove collet 22 radially inward to firmly and intimately grip carrier line 12 and prevent the carrier line from experiencing any movement during normal operation, even under pressure and temperature conditions of up to 10,000 psi and 300° C. The carrier line is formed of a material capable of withstanding the clamping forces of the split collet without collapsing.

The flow rate of the fluid passing through carrier line 12 is regulated by adjusting members 18 and 16 relative to one another by way of their cooperating threaded portions 18b and 16d.

Rotating member 18 relative to member 16, for example, so as to move member 18 toward the right relative to member 16, causes the interior surface of portion 18d (or 18c) of member 18 to bear against member 20. This force is conveyed through members 22, 24 to ferrule 14 whereby the compressive force between ferrule 14 and member 16 urges the tapered conical portion 14d of ferrule 14 against the cooperating tapered surface 16e to cause the outlet end of passageway 14b to be altered, i.e. compressed inwardly, thereby simply and yet highly accurately regulating the flow rate. These compressive forces further provide a zero dead volume fluid-tight seal in the region of the engaging surfaces of the conical-shaped portion 14d and tapered recess 16e causing the fluid being regulated by controlling the size of passageway 14b, to pass only through outlet passageway 16b for collection by a detector or a sample collection device, for example.

It can clearly be seen that the adjustments for regulating flow rate and creating the seal between ferrule 14 and carrier line 12 and for firmly gripping carrier line 12 to prevent movement thereof are totally independent of one another.

It can thus be seen that the present invention provides a durable variable restrictor which minimizes clogging and is easily adjusted for flow rates over a wide pressure/density range. The simplicity of the system enables the automated device to maintain constant flow over wide parameter changes.

A latitude of modification, change and substitution is intended in the foregoing disclosure and in some instances, some features of the invention will be employed without a corresponding use of other features. Accordingly, it is appropriate that the appended claims be construed broadly and in a manner consistent with the spirit and scope of the invention herein described.

What is claimed is:

1. Flow control means comprising:
   an elongated hollow tubular member for conveying a fluid;
   a hollow housing having one closed end provided with an outlet substantially aligned with the longitudinal axis of said tubular member;
   said hollow housing receiving and surrounding one end of said tubular member and having a tapered recess along the interior of said closed end;
   a yieldable member having an elongated opening extending along the longitudinal axis of said yieldable member and a forward tapered portion extending into said tapered recess and having a rearward portion;
   the rearward end of the opening in said yieldable member being of enlarged diameter to receive the end of said elongated tubular member extending into said housing;
   first means being adjustable for urging the tapered end of said yieldable member into said tapered recess for simultaneously providing a fluid-tight seal therebetween and for compressing said tapered forward end to thereby control the size of the opening at the forward end of said yieldable member; and second means being adjustable for urging said rearward end of said yieldable member into firm engagement with said hollow tubular member, said first and second means being independently adjustable.

2. The apparatus of claim 1 wherein said housing comprises a hollow substantially cylindrical-shaped member enclosed at a first end thereof and provided with an elongated opening aligned with the longitudinal axis of said housing, said tapered recess being formed in the interior surface of the closed end of said housing;

said opening in said housing extending through said closed end and being of a diameter substantially equal to the internal diameter of said hollow tubular means and being substantially aligned with the longitudinal axis of said elongated tubular means;

second substantially cylindrical-shaped means being threaded about a first surface thereof for threaded engagement with the threaded portion provided in said housing means and being hollow so as to accommodate one end of said second means;

one end of said second means being provided with an opening;

said elongated tubular member extending through and being displaced from said opening in said second means.

3. The apparatus of claim 2 wherein said second means is an end cap comprised of a cylindrical portion threaded along its exterior surface and closed at one end, said closed end having a clearance opening through which said hollow member extends.

4. The apparatus of claim 3 wherein the opening in said end cap is greater than the outer diameter of said elongated tubular member to provide sufficient clearance between said elongated tubular member and said end cap.

5. Flow control means comprising:

an elongated hollow tubular member for conveying a fluid;

a hollow housing having one closed end provided with an outlet substantially aligned with the longitudinal axis of said tubular member;

said hollow housing receiving and surrounding one end of said tubular member and having a tapered recess along the interior of said closed end;

a yieldable member having an elongated opening extending along the longitudinal axis of said yieldable member and a forward tapered portion extending into said tapered recess and having a rearward portion;

the rearward end of the opening in said yieldable member being of enlarged diameter to receive the end of said elongated tubular member extending into said housing;

first means being adjustable for urging the tapered end of said yieldable member into said tapered recess for simultaneously providing a fluid-tight seal therebetween and for compressing said tapered forward end to thereby control the size of the opening at the forward end of said yieldable member; and second means arranged within said first means and being adjustable to urge the rear end of said yieldable member into firm engagement with said second means and with the portion of said elongated tubular member extending into the rearward end of said yieldable member to provide a fluid-tight seal between said yieldable member and said elongated tubular member and between said yieldable member and said second means.

6. The apparatus of claim 5 wherein said second means further comprises second yieldable means surrounding said elongated tubular member and being contracted by said adjustable second means for firmly gripping said tubular member, said gripping force being a function of the adjustment of said second means.

7. The apparatus of claim 5 wherein said first and second means are independently adjustable.

8. The apparatus of claim 2 wherein said second means comprises a second elongated hollow housing having an inwardly directed flange at one end thereof, said second elongated hollow housing being positioned within first-mentioned said hollow housing;

the end of said second elongated hollow housing opposite the end having said flange being provided with a threaded portion along the interior surface thereof;

a third elongated hollow housing extending into said second elongated hollow housing;

said elongated tubular member being open at both ends and extending through said third elongated hollow housing;

said third elongated hollow housing being open at both ends and having a threaded portion along its exterior surface for threadedly engaging the interior threaded portion of said second elongated hollow housing and having a tapered recess for engagement with the rear end of said yieldable member;

whereby adjustment of said second elongated hollow housing relative to said third hollow housing urges the rearward end of said yieldable member into firm engagement with said elongated tubular member.

9. The apparatus of claim 8 wherein the rearward end of said yieldable member has a tapered configuration generally conforming to the tapered recess of said third elongated hollow housing.

10. The apparatus of claim 9 wherein the forward end of said first yieldable member extends through the opening in said second elongated hollow housing formed by said inwardly directed flange;

said first yieldable member having an annular shoulder engaging said inwardly directed flange to limit the movement of said first yieldable member in a first predetermined direction relative to said second hollow cylindrical member.

11. The apparatus of claim 8 further comprising a second hollow, tapered yieldable member surrounding said elongated tubular member, the tapered portion thereof engaging the tapered recess in said third elongated hollow housing;

a rigid, hollow member having a first end engaging said first yieldable member and a second end engaging said second yieldable member;

said first end having a tapered recess receiving the tapered rear end of said second yieldable member, whereby upon adjustment of said second and third hollow housing relative to one another, said first yieldable member forms a seal with said rigid member and said second yieldable member is contracted to firmly grip said elongated tubular member extending therethrough.

12. Apparatus for joining a hollow tubular carrier line to a ferrule comprising:
- a first hollow housing with an inwardly directed flange at one end defining an opening of reduced diameter;
- said ferrule having a forward portion of reduced diameter relative to the rearward portion thereof to define a shoulder therebetween;
- said forward end of said ferrule extending through the opening in said first housing with said shoulder engaging said flange;
- a second hollow housing extending into said first housing and having an elongated central opening receiving said carrier line, said opening at the end of the second hollow housing adjacent said ferrule being gradually enlarged and defined by a tapered recess at the end thereof extending into said first hollow housing;
- said first and second housing having cooperating threaded portions along opposing surfaces thereof for threaded engagement to adjust the positions of said first and second housing relative to one another;
- said ferrule rearward portion having a gradually tapered conical-shaped exterior surface which conforms to the conical-shaped recess in said second hollow housing and being compressed inwardly upon adjustment of said first and second housings; and
- said ferrule having an opening at the rearward end thereof for receiving one end of said hollow tubular carrier line whereby the compressed ferrule firmly grips said tubular carrier line.

13. Apparatus for joining a hollow tubular carrier line to a ferrule comprising:
- a first hollow housing with an inwardly directed flange at one end defining an opening of reduced diameter;
- said ferrule having a forward portion of reduced diameter relative to the rearward portion thereof to define a shoulder therebetween;
- said forward end of said ferrule extending through the opening in said first housing with said shoulder engaging said flange;
- a second hollow housing extending into said first housing and having a tapered recess at the end thereof extending into said first housing;
- said first and second housings having cooperating threaded portions along opposing surfaces thereof for threaded engagement to adjust the positions of said first and second housings relative to one another;
- said ferrule rearward portion being tapered and being compressed inwardly upon adjustment of said first and second housings;
- said ferrule having an opening at the rearward end thereof for receiving one end of said hollow tubular carrier line whereby the compressed ferrule firmly grips said tubular carrier line;
- a hollow split holding collet having a tapered end engaging the tapered recess in said second housing; and
- adapter means positioned between said collet and said yieldable ferrule and cooperating with said collet and said first and second housing for compressing said yieldable ferrule and said collet for retaining the carrier line against movement when said first and second hollow housings are properly adjusted; and
- said tubular member extending through said second housing and said collet and said adapter and extending into the rearward end of said ferrule.

14. The apparatus of claim 13 further comprising adjustable compressing means for compressing the forward end of said ferrule, said ferrule having a tapered forward end and an opening extending through said ferrule, said adjustable compressing means including an outlet for receiving fluid delivered by said ferrule.

* * * * *